(12) United States Patent
Schlesser

(10) Patent No.: US 7,771,756 B1
(45) Date of Patent: Aug. 10, 2010

(54) NUTRITIONAL SUPPLEMENT TO ENHANCE LEARNING, ACADEMIC, AND BEHAVIORAL FUNCTIONING

(76) Inventor: Jerry L. Schlesser, 24800 SW. Valley View Rd., West Linn, OR (US) 97068

(*) Notice: Subject to any disclaimer, the term of this patent is extended or adjusted under 35 U.S.C. 154(b) by 649 days.

(21) Appl. No.: 11/154,914

(22) Filed: Jun. 16, 2005

(51) Int. Cl.
*A61K 36/00* (2006.01)
*A61K 31/00* (2006.01)
(52) U.S. Cl. .......................... 424/725; 514/1
(58) Field of Classification Search ........... None
See application file for complete search history.

(56) References Cited

U.S. PATENT DOCUMENTS

| | | | |
|---|---|---|---|
| 4,698,360 A | 10/1987 | Masquelier | |
| 6,733,797 B1 | 5/2004 | Summers | |
| 2002/0182196 A1 | 12/2002 | McCleary | |
| 2003/0104080 A1* | 6/2003 | Singh et al. | 424/729 |
| 2005/0004046 A1 | 1/2005 | Praag et al. | |

OTHER PUBLICATIONS http://www.findarticles.com/p/articles/mi_go2672/is_200303/ai_n7572424. Oberer J.J. Effects of learning-style teaching on elementary students' behaviors, achievements and attitudes. 2003.*
Carlton RM, Ente G, Blum L, Heyman N, Davis W, Ambrosino S. Altern Therap Health Med. 2000; 6(3), 85-91.*
http://web.archive.org/web/*/http://www.advantig.net/potential.html (Date Posted on Web: Oct. 11, 2004). Date Accessed: Sep. 13, 2006.*
http://www.findarticles.com/p/articles/mi_go2672/is_200303/ai_n7572424. Oberer J.J. Effects of learning-style teaching on elementary students' behaviors, achievements and attitudes. 2003.*
Carlton RM, Ente G, Blum L, Heyman N, Davis W, Ambrosino S. Altern Therap Health Med. 2000; 6(3), 85-91.*
Schoenthaler, S.J. & Bier, I.D., The effect of vitamin-mineral supplementation on juvenile delinquency among American schoolchildren: a randomized, double-blind placebo-controlled trial. J Altem. Complement Med. Feb. 2000;6(1):7-17. Mary Ann Liebert, Inc., New Rochelle NY.
Schoenthaler, S.J. et.al., The effect of vitamin-mineral supplementation on the intelligence of American schoolchildren: a randomized, double-blind placebo-controlled trial. J Altern. Complement Med. Feb. 2000;6(1):19-21. Mary Ann Liebert, Inc., New Rochelle NY.
Schoenthaler,, SJ., Effect of Nutrition on Crime, Intelligence, Academic, Performance, and Brain Function. Paper presented at 15th International Conference on Human Function. Sep. 22-22, 2000, Wichita, KS.

* cited by examiner

*Primary Examiner*—Christopher R. Tate
*Assistant Examiner*—Amy L Clark
(74) *Attorney, Agent, or Firm*—Bert P. Krages, II

(57) ABSTRACT

A nutritional supplement to improve learning, academic, and behavioral performance, particularly of children in academic settings, comprising a quantity of flavonoid compounds with oxygen radical absorbance capacity (ORAC) derived from a multitude of plant substances, lipoic-carotenoid compounds, and a neurotransmitter amino acid.

10 Claims, No Drawings

NUTRITIONAL SUPPLEMENT TO ENHANCE LEARNING, ACADEMIC, AND BEHAVIORAL FUNCTIONING

CROSS-REFERENCED TO RELATED APPLICATIONS

None

FEDERALLY SPONSORED RESEARCH

No

SEQUENCE LISTING OR PROGRAM

Not Applicable

BACKGROUND OF THE INVENTION

It is well known that nutrition plays an important role in academic performance and several studies have observed significant links between the consumption of nutrients such as vitamins, minerals, and phytochemicals and classroom achievement, conduct, and basic intelligence. (Schoenthaler S. J., "Effect of Nutrition on Crime, Intelligence, Academic Performance, and Brain Function" paper presented at 15th International Conference on Human Function, Sep. 22-24, 2000, Wichita, Kansas). Despite efforts by federal and state government agencies to improve the quality of nutrition during childhood, the majority of children fail to obtain sufficient nutrition to perform their best when at school. According the U.S. Department of Agriculture, children are facing a health crisis with regard to nutrition and exercise. Few are meeting the Dietary Guidelines for Americans and many fail to eat healthy foods and are physically inactive. The Centers for Disease Control reported that a survey in 2003 revealed that only 22 percent of high school students had consumed the recommended five daily servings of fruits and vegetables (excluding fried-potato products) during the previous seven days.

Another issue associated with poor nutrition is the lack of student discipline. This has become one of the most serious problems facing the nation's educational system and can be found in many school environments. The most common form is the minor kind of misbehavior that disrupts classroom activities and interferes with learning. It is estimated that about one-half of classroom time in American schools is taken up with activities other than instruction, and disciplinary problems are responsible for a large part of this lost time.

There exists a need for nutritional supplements and methods for their use that enhance academic and behavioral performance of children in academic settings by improving their nutrition. The present invention satisfies this need and is also effective in improving learning and behavior in other settings and among other age groups.

SUMMARY OF THE INVENTION

A nutritional supplement to improve learning, behavioral and academic performance, particularly of children in academic settings, comprising a quantity of flavonoid compounds with oxygen radical absorbance capacity (ORAC) derived from a multitude of plant substances in combination with lipophilic antioxidants in the form of lipoic-carotenoid compounds, a neuro-transmitter amino acid or derivative, and preferably, in combination with essential vitamins and minerals.

DESCRIPTION OF THE INVENTION

It has been found that a nutritional supplement consisting of flavonoid compounds, lipoic-carotenoid compounds, and a neurotransmitter amino acid such as taurine, taken at a frequency of once per day, is particularly useful in improving the ability to learn in people, particularly with respect to the academic, behavioral, and emotional functioning of children in a school setting. Learning in the context of the invention can be considered to encompass increasing knowledge, comprehension, calculation, and the ability to analyze and evaluate the subject matter. In academic settings, learning is often assessed by performance measures such as standardized testing of reading and mathematical skills. Behavioral performance refers to behavior that encompasses self-control, facilitates better relationships between people, and that fosters conditions that enable students in a classroom environment to learn more efficiently and effectively. In many cases, improved behavioral performance manifests itself in the form of individuals exercising better judgment with regard to decisions that affect their relationships with other people and a readiness to learn. In academic settings, such judgments encompass decisions to refrain from impulsive actions that create disorder in classrooms.

One of the features of the invention is that the composition comprises extracts or concentrates of antioxidant compounds prepared from multiple plant species and thus ensures a broad base of compounds that contribute to its overall antioxidant capabilities. For example, dietary flavonoids such anthocyanins, catechins, flavonols, and proanthocyanidins can be extracted from the fruits of *Vaccinium* species (e.g., bilberry, blueberry, cranberry, and huckleberry), Prunus species (e.g., cherry, plums, prunes, and apricots), *Malus* species (e.g., apples), *Rubus* species (e.g., raspberry and blackberries), *Garcinia*, and *Theobroma* species (e.g., cacao); and the leaves of plant species such as *Camellia sinensis*. Flavonones such as hespertin and naringenin can be extracted from the fruits of *Citrus* species. The combination of the compounds extracted from these plant species act to improve the nutritional status of children and enable them to perform better at reading comprehension, mathematical computations, and maintaining emotional self-control.

Flavonoid and lipoic-carotenoid compounds are well recognized as potent antioxidants but encompass a substantial degree of variation with respect to biochemical behavior. Specific compounds in these nutrient classes tend to exert their antioxidant capacity in either predominantly aqueous or lipid-based biochemical environments and deriving them from multiple plant species ensures that compounds with hydrophilic and lipophilic affinities are incorporated into the nutritional supplement. Another problem addressed by formulating the supplement with extracts or concentrates from several plant species is that it reduces the possibility of inadvertently underformulating the antioxidant content because of natural variations of antioxidant content within a single species. Because these compounds are produced by plants, they can be found in different concentrations among different genotypes within the same plant species. This fact suggests that the potential efficacy of combinations of antioxidants may vary considerably from genotype to genotype. Likewise, the form in which a specific nutrient exists will affect its bioavailability. For example, the bioavailability of quercetin is known to differ among food sources depending on the type of glycosides they are bound in. The incorporation of antioxidant substances from multiple plant species thus helps to ensure a base of antioxidants that is more biochemically complete than is the case with supplements that are made from a more limited number of source materials.

Another important consideration regarding the invention is that it is designed to be effective for a broad population. Individuals vary significantly in their ability to absorb and process specific nutrients. A significant factor is the normal individual genetic variability among populations with regard to the enzymes and transporters that carry out the functions of metabolism. These factors may determine the normal baselines of specific nutrients in an individual's body as well as how efficiently they absorb, metabolize, and excrete those nutrients. In addition, the bioavailability of antioxidants can depend on the specific nature of an individual's diet. For example, nutrients such as lutein esters tend to be absorbed more efficiently when consumed in the presence of certain levels of fat or in the presence of ascorbic acid. Because institutions such as schools typically have little to no control over the diet outside the institutional setting, it is important that a nutritional supplement be formulated so that the nutrients are sufficiently bioavailable to heterogenous populations that experience widely-different diets and metabolisms. A supplement that encompasses a broad base of source materials is better able to ensure a level of uptake that is capable of producing the desired nutritive effect throughout a diverse population.

By incorporating a broad base of antioxidants, the supplement sustains its effectiveness over a period of several hours because the kinetic characteristics of the constituents cover a significant range of biochemical uptake, activity, and elimination. This addresses a shortcoming of those supplements that consist primarily of only a few antioxidant compounds because the absorption and effective period of such supplements may not be sufficient to sustain the desired action throughout the course of the relevant period, such as a school day, without the need to administer the supplement two or more times per day. Combining antioxidants that have different rates of metabolic processing thus enables the supplement to work effectively over an extended period of time.

The supplement also contains one of the neurotransmitter amino acids such as gamma-aminobutyric acid (GABA), glutamic acid, glycine, lysine, methionine, phenylalanine, serine, taurine, theonine, tryptophane, and tyrosine (or their respective precursor and derivative compounds). These substances act to regulate the flow of information throughout the brain, either directly or by facilitating the formation of substances that have regulating effects. For example, taurine is a conditionally-essential amino acid that is considered to be a mild-inhibitory neuro-transmitter that exerts a balancing effect on nerve impulses. Although humans naturally produce taurine after maturing past infancy, they are not always able to synthesize enough to meet demands when subjected to stress or nutritional deficiency. In such cases, supplemental administration of taurine can produce improved attention and verbal reasoning. Taurine may be taken up by the body through the diet and may also be synthesized derivatively from other amino acids such as cysteine or methionine. Therefore, precursor and derivative compounds can serve as supplements that are similar in effectiveness to the more basic forms of these amino acids. For example, n-acetylcysteine is a well known derivative of cysteine, 5-hydroxytryptophan (5-HTP) is a well known derivative of tryptophane, and glutathione is a well known tripeptide composed of glutamic acid, cysteine and glycine.

The following example of the administration of a nutritional supplement in an academic setting is illustrative of how the invention is effective at improving academic and behavioral performance. During the 2003-04 school year, an elementary school in Leavenworth, Kansas instituted a program designed to evaluate the effects of improving the nutrition of its students.

This school had a diverse student body consisting of 51.2 percent Caucasians, 40.9 percent African-Americans, 7.0 percent Hispanic, and 0.9 percent of other racial and ethnic identities; and about 55 percent of the students came from economically-disadvantaged families. Prior to the 2003-04 school year, the school had a poor reputation for academic performance and student disciplinary behavior. As part of the study, about 70 percent of the 328 students enrolled at the school were provided with the preferred embodiment of the invention in a chewable tablet form. Academic and behavioral performance as measured by Grade 5 reading standardized assessment scores, Grade 4 math standardized assessment scores, and parameters related to student behavior, were observed to improve markedly from those measured during the previous academic year. The improvements by performance category are summarized as follows:

|  | Exemplary | Advanced | Proficient | Basic | Unsatisfactory |
| --- | --- | --- | --- | --- | --- |
|  | Grade 5 Reading | | | | |
| 2002-03 | 14.6% | 19.5% | 22.0% | 22.0% | 22.0% |
| 2003-04 | 18.8% | 28.1% | 18.8% | 18.8% | 15.6% |
|  | Grade 4 Math | | | | |
| 2002-03 | 6.7% | 20.0% | 20.0% | 31.1% | 22.2% |
| 2003-04 | 48.1% | 25.9% | 18.5% | 3.7% | 3.7% |

| | Discipline and Behavior | | | |
| --- | --- | --- | --- | --- |
|  | Students Expelled | Students Suspended | Violent Incidents Against Students | Violent Incidents Against Staff |
| 2002-03 | 1 | 30 | 9.3 per 100 | 0.4 per 100 |
| 2003-04 | 0 | 8 | 2.8 per 100 | 0.0 per 100 |

The percentage of students at this school classified as proficient or better in reading skills increased from 56.1 percent during the 2002-03 school year to 65.5 percent during the 2003-04 school year. For math skills, the respective increase was from 46.7 percent to 92.5 percent. Serious incidents of student misbehavior decreased by more than two-thirds during the year that the supplement was administered.

DESCRIPTION OF THE PREFERRED EMBODIMENT

The present invention has a composition that comprises multiple antioxidants derived from a plurality of sources that are rich in compounds with antioxidant properties. The preferred embodiment of the invention comprises the following groups of nutritional substances:

a group of flavonoid compounds containing proanthocyanidins B1 through B4 in free and esterified form including gallic acid, catechin, epicatechin, cyanidin, quercetin, procyanidolic oligomers and polymers, malvidin, petunidin, rutin, epigallocatechin gallate (EGCG), delphinidin, naringin and carnosic acid; which are derived from grape, citrus, decaffeinated green tea, bilberry, blueberry, cherry, cranberry, elderberry, raspberry, rose hips, strawberry, and red Concord grapeskin;

a group of lipoic-carotenoid compounds consisting of alpha-lipoic acid, alpha-carotene, beta-carotene, lutein, lycopene, astaxanthin, cryptoxanthin & zeaxanthin;

taurine, which is an amino acid;

tocotrienol rice bran complex (rice tocotrienols with stabilized rice bran extract); and vitamins and minerals.

Specific ingredients contained in the preferred embodiment are as follows:

| PREFERRED FORMULATION | |
|---|---|
| COMPONENT | DOSE PER TABLET |
| blended extracts and concentrates of grape, citrus, bilberry, blueberry, cherry, cranberry, elderberry, raspberry, rose hips, strawberry, and red Concord grapeskin | 300 mg |
| decaffeinated green tea extract | 12.5 mg |
| Lipoic-Carotenoid compounds | 7.5 mg |
| tocotrienol rice bran complex | 7.5 mg |
| Vitamin A (Palmitate) | 1625 IU |
| Vitamin A (beta-carotene w/mixed carotenoids) | 875 IU |
| Vitamin C (Ascorbic acid) | 190 mg |
| Vitamin C (Ascorbyl palmitate) | 10 mg |
| Vitamin D-3 (Cholecalciferol) | 200 IU |
| Vitamin E (d-alpha tochopherol with mixed tocopherols) | 15 IU |
| Vitamin K (Phytonadione) | 40 mcg |
| Vitamin B-1 (Thiamin HCl) | 0.75 mg |
| Vitamin B-2 (riboflavin R5' phosphate complex) | 0.85 mg |
| Vitamin B-3 (Niacinamide/Niacin complex) | 10 mg |
| Vitamin B-6 (Pyridoxine P5' phosphate complex) | 1 mg |
| Folate (Folic acid) | 200 mcg |
| Vitamin B-12 (Cyano & methylcobalamin complex) | 3 mcg |
| Biotin USP | 150 mcg |
| Pantothenic acid (Calcium pantothenate) | 5 mg |
| Calcium (Carbonate/citrate/malate) | 50 mg |
| Iron (Non-Heme iron from Pyrophosphate) | 9 mg |
| Iodine (Potassium iodide) | 75 mcg |
| Magnesium (citrate/oxide/krebs acids) | 25 mg |
| Zinc (Citrate-oxide-lactate complex) | 2.5 mg |
| Selenium (Selenomethionine AAC Complex) | 35 mcg |
| Copper (Citrate) | 325 mcg |
| Manganese (Glycinate/carbonate complex) | 1 mg |
| Chromium (Glycinate/polynicotinate complex) | 60 mcg |
| Molybdenum (Citrate AAC complex) | 37.50 mcg |
| Silicon (Dioxide) | 2.25 mg |
| Taurine | 50 mg |

The flavonoid and lipoic acid-carotenoid compounds are intended to provide the supplement with a high level of antioxidant capacity when consumed. Antioxidant capacity is generally defined as the ability of a compound or group of compounds to reduce reactive oxygen species. One means of measuring antioxidant capacity is Oxygen Radical Absorbance Capacity (ORAC). Tocotrienols, like flavonoid and lipoic acid-carotenoid compounds, are also recognized as potent antioxidants and may be usefully incorporated into the supplement. Vitamins and minerals have been found to contribute to academic and behavioral performance and likewise may be usefully incorporated into the nutritional supplement. In the preferred embodiment, commonly supplemented vitamins and minerals should be provided in amounts equivalent to 10 to 100% of the Reference Daily Intakes (RDIs) as established by the U.S. Food and Drug Administration.

The preferred regimen for children in a school setting is that the invention be consumed in a chewable tablet form once per day during lunchtime during the entire school year. In the preferred formulation described above, each child would consume two tablets per day. The exact time of the administration is not critical because the nutrient concentration in subjects will gradually climb to a static level over the course of several days following the commencement of the administration. So long as the supplements are consumed five days per week, the nutrient concentrations will maintain themselves at an effective level.

The invention can be used in other institutional settings such as juvenile correctional facilities with a similar or identical regimen. Furthermore, is should be emphasized that the regimen does not require institutional administration and could be implemented by parents or guardians of children outside the confines of an institutional program. Likewise, the supplement and regimen will have the effect of improving behavioral and academic performance when used by adults.

The active ingredients can be mixed with a carrier and be manufactured and administered in forms such as tablets, capsules, food bars, powders, lozenges, emulsions, solutions, or any means by which the active ingredients are embedded into an ingestable carrier. Such carriers include but are not limited to dextrose, sucrose, syrups, methyl cellulose, magnesium stearate, and oils. The carrier can also encompass preserving agents, sweeteners, or flavoring agents.

Although the invention has been described in detail with reference to this preferred embodiments, other embodiments can achieve the same results. Variations and modifications of the present invention will be apparent to those skilled in the art and it is intended to cover all modifications and equivalents. The entire disclosures of all references, applications, patents, and publications cited within the application are incorporated by reference. In addition, the invention is not limited to application in children in academic settings and can be used beneficially by adults and children in other settings.

I claim:

1. A method for improving the academic and behavioral performance of a human in need thereof comprising administering to said human an effective amount of a nutritional supplement comprising an effective amount of flavonoid content extracted from plant material containing the same; lipoic-carotenoid compounds; and at least one amino acid or amino-acid derivative selected from the group consisting of taurine, cysteine and derivatives, gamma-aminobutyric acid (GABA), glutamic acid and derivatives, theanine, glutathione, methionine and derivatives, serine and derivatives, tyrosine, tryptophan and derivatives, lysine, glycine, and phenylalanine.

2. The method of claim 1, werein the flavonoid content of the nutritional supplement comprises extracts or concentrates that are derived from at least three plant species.

3. The method of claim 1, wherein the flavonoid content of the nutritional supplement comprises extracts or concentrates of at least three plant species selected from the group consisting of *Camellia sinensis*, *Citrus* species, elderberry (*Sambucus* species), grape (*Vitis* species), *Garcinia* species, *Malus* species, *Prunus* species, *Ribes* species, *Rubus* species, rose hips (*Rosa* species), strawberry (*Fragaria* species), *Theobroma* species, and *Vaccinium* species.

4. The method of claim 1, wherein the lipoic-carotenoid compounds comprise at least four compounds selected from the group consisting of alpha-lipoic acid, r-lipoic acid, dihydrolipoic acid, alpha-carotene, beta-carotene, lutein, lycopene, astaxanthin, cryptoxanthin, and zeaxanthin.

5. The method of claim 1, wherein the nutritional supplement further comprises at least one vitamin.

6. The method of claim 1, wherein the nutritional supplement further comprises at least one mineral.

7. The method of claim 1, wherein the flavonoid content of the nutritional supplement comprises extracts or concentrates that are derived from at least three plant species and the nutritional supplement further comprises at least one vitamin.

8. The method of claim 1, wherein the flavonoid content of the nutritional supplement comprises extracts or concentrates that are derived from at least three plant species and the nutritional supplement further comprises at least one mineral.

9. The method of claim 1, wherein the flavonoid content of the nutritional supplement comprises extracts or concentrates of at least three plant species selected from the group consisting of *Camellia sinensis*, *Citrus* species, elderberry (*Sambucus* species), grape (*Vitis* species), *Garcinia* species, *Malus* species, *Prunus* species, *Ribes* species, *Rubus* species, rose hips (*Rosa* species), strawberry (*Fragaria* species), *Theobroma* species, and *Vaccinium* species; and further comprises lipoic-carotenoid compounds comprise at least four compounds selected from a group consisting of alpha-lipoic acid, r-lipoic acid, dihydrolipoic acid, alpha-carotene, beta-carotene, lutein, lycopene, astaxanthin, cryptoxanthin, and zeaxanthin; and wherein the nutritional supplement further comprises at least one vitamin.

10. The method of claim 1, wherein the flavonoid content of the nutritional supplement comprises extracts or concentrates of at least three plant species selected from the group consisting of *Camellia sinensis*, *Citrus* species, elderberry, grape, *Garcinia* species, *Malus* species, *Prunus* species, *Ribes* species, *Rubus* species, rose hips, strawberry, *Theobroma* species, and *Vaccinium* species; the lipoic-carotenoid compounds comprise at least four compounds selected from a group consisting of alpha-lipoic acid, r-lipoic acid, dihydrolipoic acid, alpha-carotene, beta-carotene, lutein, lycopene, astaxanthin, cryptoxanthin, and zeaxanthin; and the nutritional supplement further comprises at least one vitamin and at least one mineral.

* * * * *